(12) United States Patent
Hennig

(10) Patent No.: US 8,345,247 B2
(45) Date of Patent: Jan. 1, 2013

(54) DEVICE FOR DETECTING SIGNS OF BACTERIAL INFECTION OF THE ROOT CHANNEL OF TEETH

(75) Inventor: Thomas Hennig, Langenfeld (DE)

(73) Assignee: Ferton Holdings, S.A., Delmont (CH)

( * ) Notice: Subject to any disclaimer, the term of this patent is extended or adjusted under 35 U.S.C. 154(b) by 292 days.

(21) Appl. No.: 12/680,924

(22) PCT Filed: Oct. 1, 2008

(86) PCT No.: PCT/EP2008/008328
§ 371 (c)(1),
(2), (4) Date: May 13, 2010

(87) PCT Pub. No.: WO2009/046921
PCT Pub. Date: Apr. 16, 2009

(65) Prior Publication Data
US 2010/0221677 A1 Sep. 2, 2010

(30) Foreign Application Priority Data
Oct. 1, 2007 (DE) .......................... 10 2007 047 068

(51) Int. Cl.
G01N 21/00 (2006.01)
(52) U.S. Cl. .......................................... 356/432; 356/73
(58) Field of Classification Search ........... 356/432–436
See application file for complete search history.

(56) References Cited

U.S. PATENT DOCUMENTS

| 4,979,900 | A | | 12/1990 | Okamoto et al. | |
| 5,503,559 | A | * | 4/1996 | Vari | 433/224 |
| 2005/0232550 | A1 | | 10/2005 | Nakajima et al. | |
| 2007/0188738 | A1 | * | 8/2007 | Jung et al. | 356/73 |

FOREIGN PATENT DOCUMENTS

| DE | 3031249 A | 3/1981 |
| EP | 0862896 A | 3/1998 |
| JP | 03 112549 A | 5/1991 |

OTHER PUBLICATIONS

International Search Report dated Mar. 18, 2009 to corresponding international patent application No. PCT/EP2008/008328, 3 pages.
Pini, R. et al., "Laser Dentistry Root Canal Diagnostic Techique Based on UV-Induced Fluorescence Spectroscopy", BD. 9, Nr. 4, 1989, Seiten 358-361, XP002517905, ISSN: 0196-8092, Seite 359: "Materials and Methods".

* cited by examiner

Primary Examiner — Michael P Stafira
(74) Attorney, Agent, or Firm — Maier & Maier PLLC

(57) ABSTRACT

The invention relates to a device for detecting signs of bacterial infection of teeth, comprising a light source, a receiving unit, an evaluation unit, coupled to the receiving unit, at least one emission fiber, coupled to the light source, and at least one detection fiber, coupled to the receiving unit. The invention is characterized in that the common distal front face of the at least one emission fiber and the at least one detection fiber is connected to a front face of a flexible plastic optical wave guide, the diameter of the plastic optical wave guide being less than 400 μm, preferably less than 300 μm.

29 Claims, 4 Drawing Sheets

DEVICE FOR DETECTING SIGNS OF BACTERIAL INFECTION OF THE ROOT CHANNEL OF TEETH

RELATED APPLICATIONS

Figure 1:
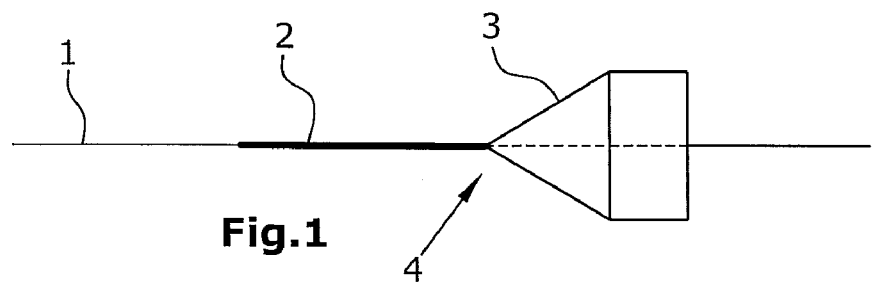

This application claims priority, under 35 U.S.C. §119, to German patent application No.: 10 2007 047 068.3, filed on Oct. 1, 2007, the disclosure of which is incorporated by reference herein in its entirety.

The invention refers to a device for detecting signs of bacterial infection of teeth as defined in the preamble of claim 1.

Such a device is known from DE-A-3031249 wherein visible luminescence is used for detecting the presence of caries in human teeth. A tooth to be examined is irradiated with almost monochromatic light. The monochromatic light excites fluorescent radiation at this tooth. The intensity of the fluorescent radiation is measured and evaluated at two different wavelengths, where the dependence of the intensity on the spectrum for caries and non-caries is about the same at one of the wavelengths, whereas, at the other wavelength, the relative intensity increases drastically in the presence of caries. Thus, a healthy tooth portion can be distinguished from a carious tooth portion in a contactless manner by detecting the fluorescent radiation of a tooth irradiated with monochromatic light.

From EP-A-0862896 another device for detecting bacterial infection is known, comprising a hand-held member including emission and detection means for the generation of an excitation radiation and for directing the same onto a tooth to be examined and for detecting and evaluating the fluorescent radiation excited at the irradiated tooth. Each emission and detection means comprises a plurality of individual emission fibers that irradiate the excitation radiation onto the tooth under examination, as well as detection fibers hat detect the fluorescent radiation excited at the irradiated tooth.

The devices known heretofore are disadvantageous in that the light guides with which the excitation radiation has been directed onto the tooth to be examined are not suited for insertion into root channels and up to their tips. Further, the optical waveguides used in prior devices are optical waveguides of silica glass with a low extensibility of less than 1%. Therefore, these optical waveguides are too rigid to follow a naturally curved root channel and easily break in the rough root channel.

However, prior to every sealing of a root channel, it is imperative that the root channel be fully free from bacteria.

It is thus an object of the invention to provide a device of the kind described above with which bacteria-infected parts in the root channel can be detected.

The object is achieved with the features of claim 1.

The invention advantageously provides that a device of the kind described above comprises a light source, a receiving unit, an evaluation unit coupled to the receiving unit, at least one emission fiber coupled to the light source, and at least one detection fiber coupled to the receiving unit. The common distal front face of the at least one emission fiber and of the at least one detection fiber is connected with a front face of a single flexible plastic optical waveguide, the diameter of the plastic optical waveguide being smaller than 400 µm, preferably less than 300 µm.

It is an advantage of this embodiment that the plastic optical waveguide can readily be inserted up to the tips of a root channel since the root channel tips generally have a diameter of between 300 µm to 400 µm. It is another advantage that, different from prior art as known heretofore, the invention uses a single optical waveguide. Preferably, the plastic optical waveguide is made of polystyrene.

This embodiment offers the additional advantage that the flexible plastic optical waveguide, since it is made of plastics, readily takes an extension by 8% and can easily follow the course of a naturally curved root channel. Further, in contrast with optical waveguides of silica glass, it is not brittle. Other than with the use of optical waveguides of silica glass, there is thus no risk of pieces of the optical waveguide remaining in the root channel from where they are difficult to remove, if they can be removed at all.

Additional advantages are that the device is easy to manufacture and guarantees easy handling and safe application. Moreover, the plastic optical waveguide is simple to replace.

In another embodiment of the invention, it is provided that the common distal front face of the emission and detection fibers and the proximal front face of the plastic optical waveguide are pressed against each other by means of spring force.

As the emission and detection fibers, seven optical waveguides (i.e. three emission and four detection fibers or four emission and three detection fibers) with a diameter of 70 µm each, or fourteen optical waveguides with a diameter of 50 µm each could be used, for instance.

The plastic optical light guide may, especially for an increase in the acceptance angle, be coated several times. The core diameter of the plastic optical waveguide may be less than 350 µm, preferably less than or equal to 250 µm. The total diameter of the plastic optical waveguide may be less than 400 µm, preferably less than 300 µm.

The core diameter of the plastic optical waveguide may be equal to or slightly larger than the total diameter of the emission and detection fibers.

Acrylates or fluoro acrylates with refraction indexes of between 1.42 and 1.49 may serve as coating material, so that a plastic optical waveguide with an acceptance angle of 48° can be realized.

According to the invention, the plastic optical waveguide can guide the excitation radiation emitted from the light source via the emission fibers to the tooth, as well as guide the fluorescent radiation coming from the tooth.

In another embodiment of the invention it is provided that the acceptance angle of the plastic optical waveguide is larger than 35°.

As an alternative, the acceptance angle of the plastic optical waveguide may be larger than 40°, preferably larger than 45°.

This offers the advantage that the plastic optical waveguide of the present invention is suited to also irradiate straight sections of narrow cavities without having to use additional optical elements. The maximum intensity achieved on a planar surface, preferably a surface perpendicular to the light exit surface of the plastic optical waveguide, is substantially higher for a device according to the invention than for devices that typically use optical waveguides of silica glass.

The acceptance angle of the emission and detection fibers may also be larger than 35°. As an alternative, the acceptance angle may also be larger than 40°, preferably larger than 45°.

The emission and detection fibers can be guided within one optical waveguide cable. The emission and detection fibers and thus the optical waveguide cable may be flexible.

According to a development it is provided that the plastic optical waveguide is guided in an inspection probe with a flexible or bent shaft and a coupling portion.

This embodiment facilitates the handling since the plastic optical waveguide can be inserted more easily into root channels, for instance, due to the flexible or bent shaft.

The shaft may be of a blunt design at the distal end. This reduces the risk of injuries.

The plastic optical waveguide may be glued in the shaft and/or the coupling portion.

The plastic optical waveguide may protrude distally from the inspection probe by 1 to 30 mm, preferably 15 to 25 mm.

The shaft of the inspection probe may be 10 to 30 mm long, while the diameter of the shaft may be smaller than 1 mm, preferably smaller than 0.7 mm. The shaft is made of plastics or metal, preferably stainless steel.

It may also be provided that the coupling portion is formed by a standardized syringe connector. The connecting portion may be provided with a space that is adapted to accommodate an elastically bent portion of the plastic optical waveguide when the plastic optical waveguide is connected with the emission and detection fibers.

The plastic optical waveguide may protrude freely proximally from the inspection probe by 10 to 30 mm.

The length of the inspection probe may be less than 10 cm, preferably less than 7 cm.

According to a development it is provided that a centering device is connected with the proximal end of the coupling portion, the plastic optical waveguide being guided in the centering device and protruding centrally from the proximal end of the centering device, wherein the plastic optical waveguide protrudes from the proximal end of the centering device by at most 2 mm.

A development is characterized in that the front faces of the plastic optical waveguide are anti-reflection coated, the anti-reflection coating being realized in the form of a moth-eye structure.

This embodiment solves the problem that reflections at light exit surfaces could interfere with the diagnosis, since the same cause a background signal beside a slight own fluorescence of the optical waveguides.

According to a development, the plastic optical waveguide may be designed as a replaceable tip, especially as a disposable article. This is advantageous in that the plastic optical waveguide does not have to be sterilized after each use.

In another embodiment it is provided that the inspection probe is connected with a hand piece and that the junction of the common front face of the emission and detection fibers and the front face of the plastic optical waveguide is situated within this hand piece.

This has the advantage that the handling of the device is improved, since the plastic optical waveguide can be guided better because of the hand piece.

According to a development, the light source may be arranged within the hand piece, with the total length of the at least one emission fiber and the plastic optical waveguide being less than 60 cm, preferably less than 10 cm.

This embodiment offers the advantage that the excitation radiation does not have to travel a long way. Therefore, the intensity loss of the excitation radiation can be reduced.

The following is a detailed description of embodiments of the invention with reference to the drawings.

Figure 2:
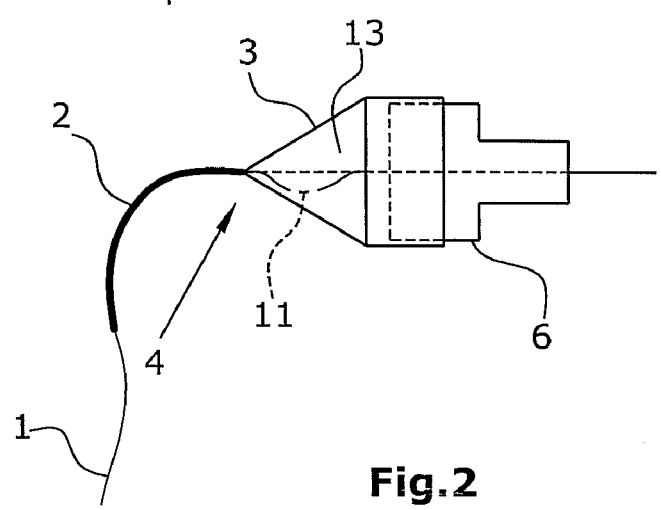
Figure 3:
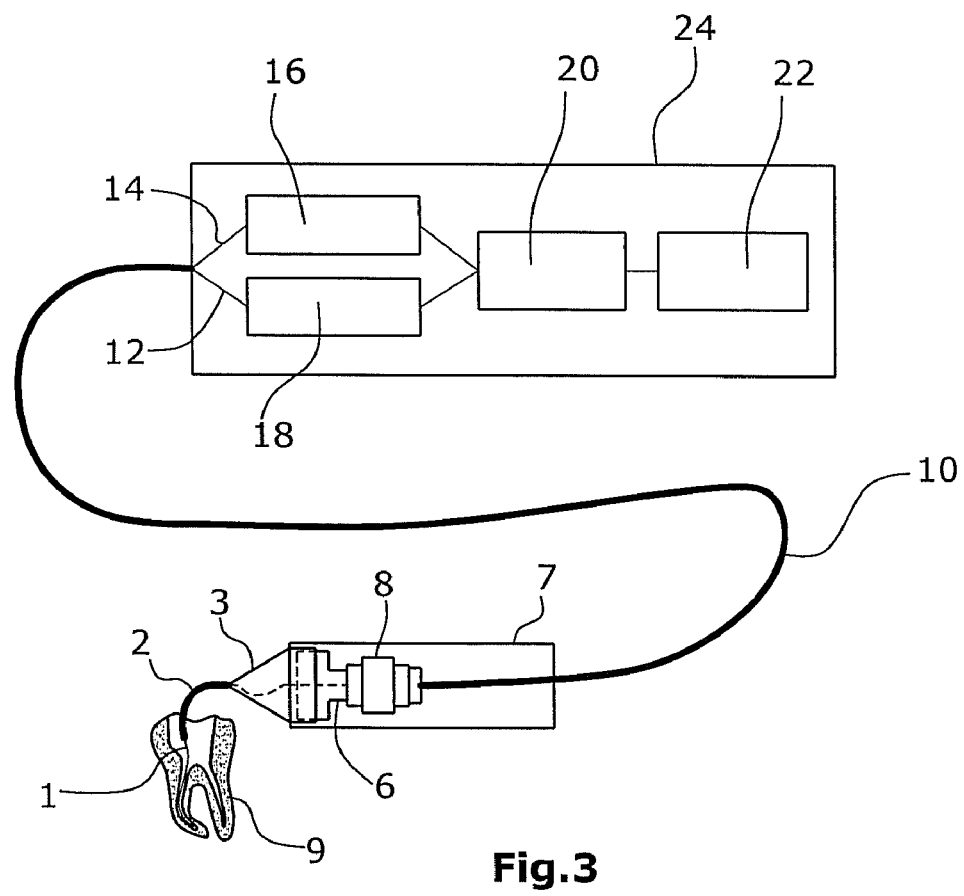
Figure 4A:
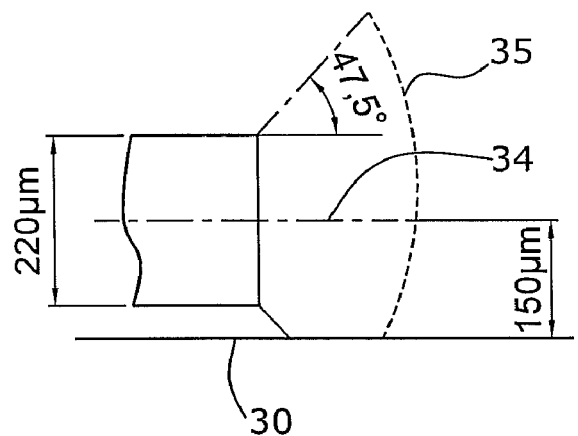
Figure 4B:
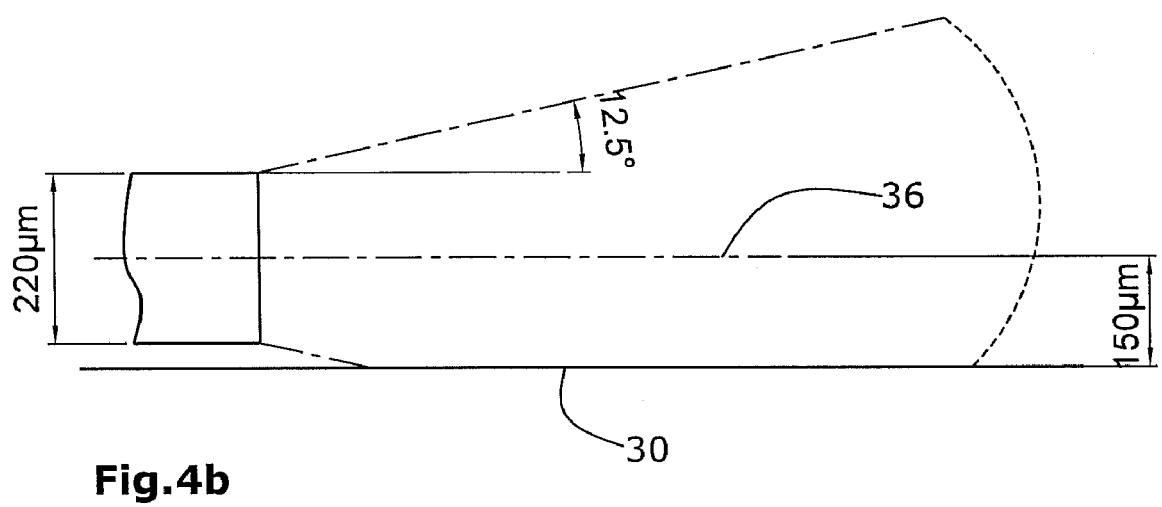
Figure 5:
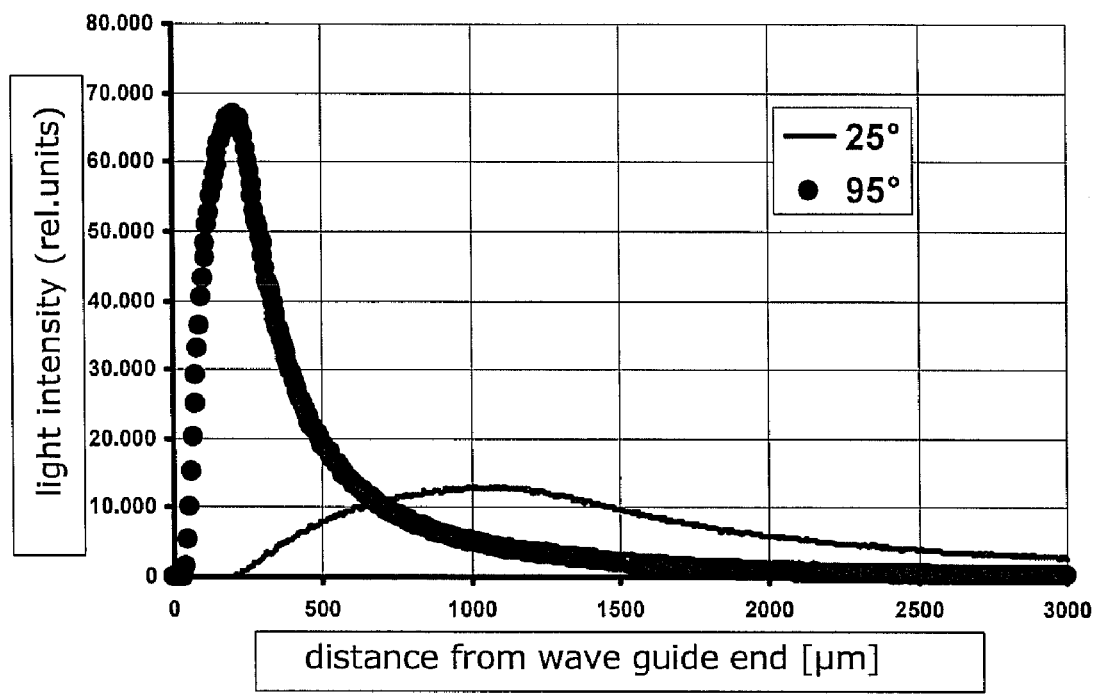
Figure 6:
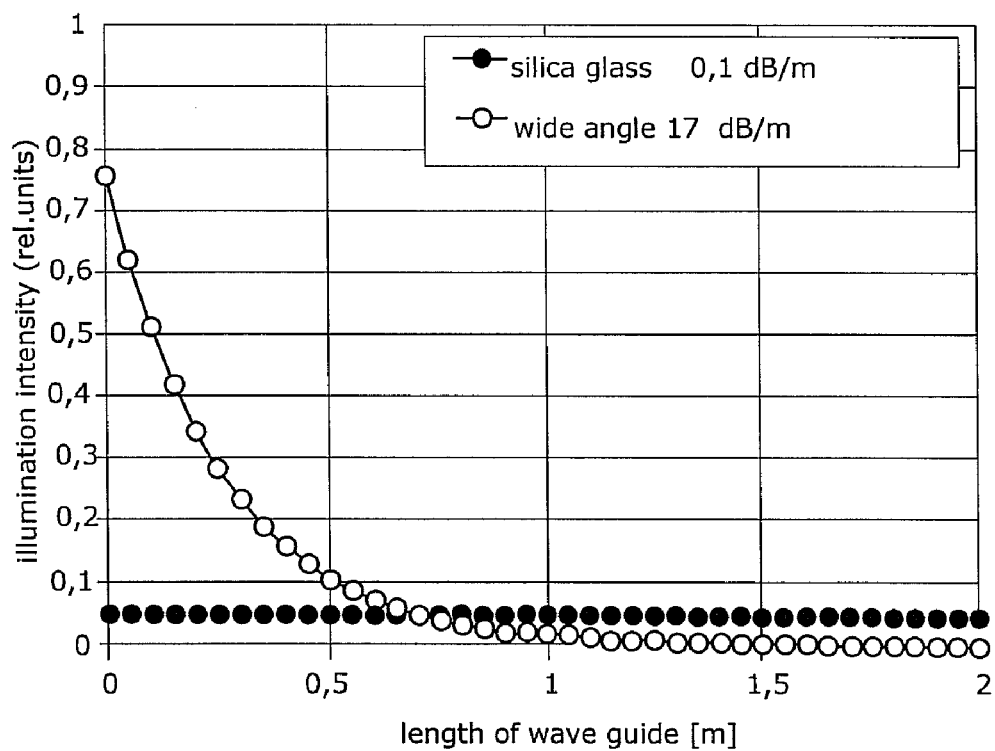
Figure 7:
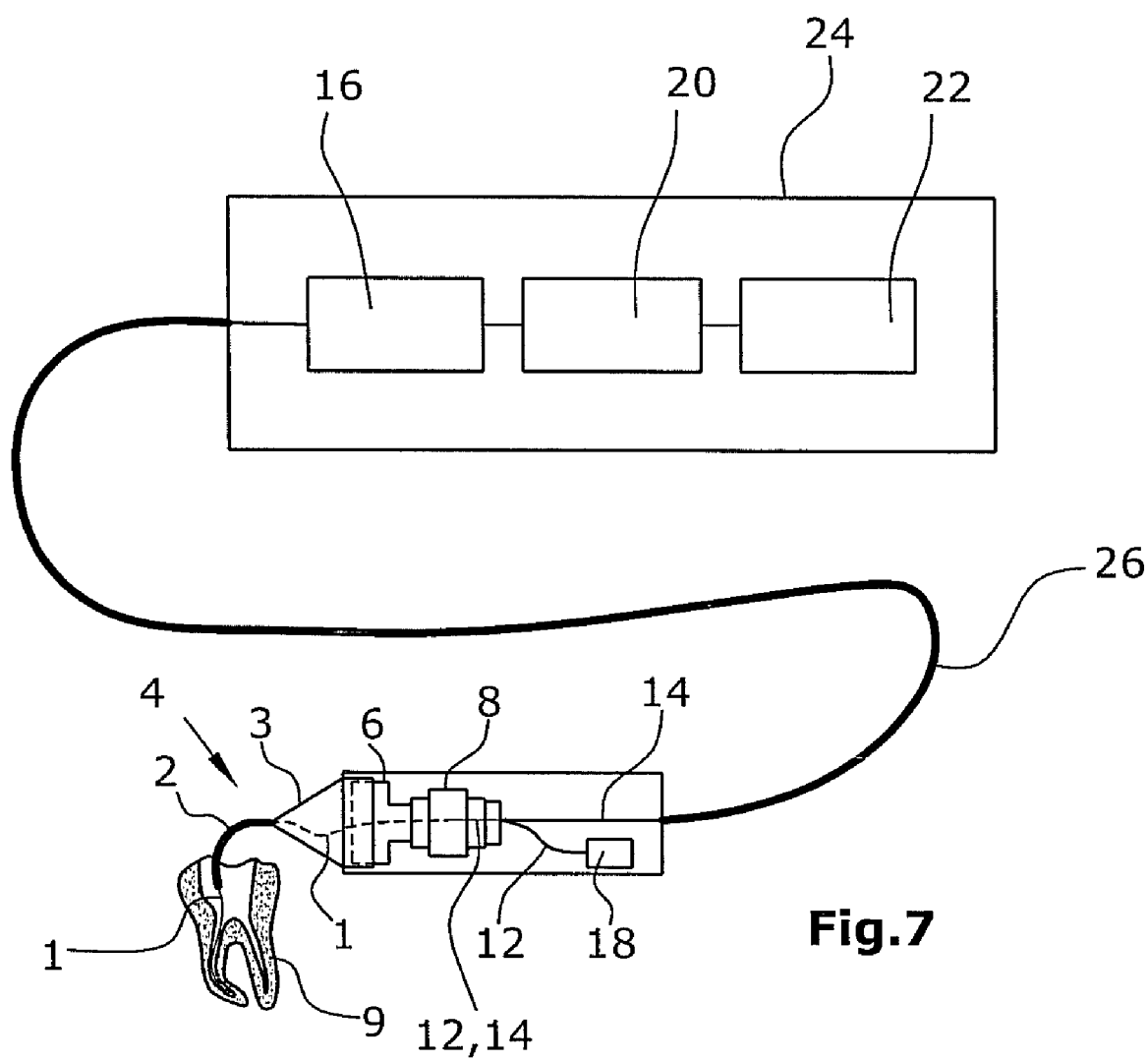

The Figures schematically show:

FIG. 1 a side elevational view of an inspection probe in which a bundle of emission and detection fibers is guided, FIG. 2 a side elevational view of an inspection probe with a curved shaft and a centering device, FIG. 3 a schematic block diagram of a device according to the invention, FIG. 4a a wide angle optical waveguide, whose axis is aligned in parallel with a planar surface, FIG. 4b an optical waveguide of silica glass, which is no wide angle optical waveguide and whose axis is aligned in parallel with a planar surface, FIG. 5 an illustration showing the distribution of light on the planar surface of FIG. 4a and FIG. 4b, FIG. 6 an illustration of the relationship between the attenuation of the illumination intensity and the length of the optical waveguide, FIG. 7 a schematic block diagram in which the light source is arranged in the hand piece.

FIG. 1 illustrates an inspection probe 4. A plastic optical waveguide 1, which is specifically used for the examination of root channels, is guided in an inspection probe 4. The inspection probe 4 comprises a shaft 2 and a coupling portion 3. The plastic optical waveguide 1 protrudes distally beyond the shaft 2 by 1-30 mm. Proximally, the plastic optical waveguide 1 protrudes beyond the coupling portion 3 by 10-30 mm. The plastic optical waveguide 1 is preferably coated once or a plurality of times. The total diameter of the plastic optical waveguide 1 is less than 400 µm, preferably less than 300 µm. The core diameter is less than 300 µm, with the core diameter preferably being 250 µm. The plastic optical waveguide 1 is preferably made from polystyrene having a refraction index of 1.6. The shaft 2 is preferably made of metal or plastic material and is advantageously made to be flexible. A user may bend it in the manner of a plastic deformation to permanently take a desired shape so as to guarantee an easy access to a root channel. The plastic optical waveguide 1 preferably is a wide angle optical waveguide having an acceptance angle larger than 35°.

FIG. 2 illustrates the inspection probe 4 of FIG. 1 with a bent shaft 2. The plastic optical waveguide 1 is fixed or glued in the shaft 2 and/or at the distal end of the coupling portion 3. A separate centering device 6 is connected at the proximal end of the coupling portion 3. The plastic optical waveguide 1 is guided within the centering device 6 and protrudes from the proximal end of the centering device 6. It protrudes by less than 2 mm and more than 0 mm. This is necessary to guarantee a direct contact between the plastic optical waveguide 1 and the optical waveguide cable 10, since the proximal end of the centering device 6, and thus the proximal end of the plastic optical waveguide 1, and the common distal end of the emission and detection fibers are pressed against each other by means of a spring. When the centering device 6 and thus the plastic optical waveguide 1 are in contact with the bundle formed by the emission fibers 12 and the detection fibers 14, the plastic optical waveguide 1 is pushed back into the coupling portion 3 for the length it protrudes proximally beyond the centering device 6. The plastic optical waveguide 1 can compensate for the change in length by elastic bending within the coupling portion 3, with the bent part 11 of the plastic optical waveguide 1 being deflected into a space 13 and generating a restoring force.

FIG. 3 illustrates a general block diagram of a device of the invention. An apparatus 24 comprises a light source 28, a receiving unit 16, an evaluation unit 20 and a display unit 22. The radiation from the light source 18 is preferably amplitude modulated, the modulation being effected with 2 kHz, for instance. The radiation from the light source 18 is coupled into emission fibers 12. The emission fibers 12 are guided in an optical guide wave cable 10 together with the detection fibers 14. The distal front face of the bundle of emission fibers 12 and detection fibers 14 is connected with the proximal front face of a plastic optical waveguide 1. The plastic optical waveguide 1 is guided within an inspection probe 4 described in FIGS. 1 and 2. The core diameter of the plastic optical waveguide 1 is larger than or equal to the total diameter of the emission fibers 12 and the detection fibers 14. As described in FIG. 2, the plastic optical waveguide 1 is guided in a centering device 6 and protrudes from the proximal end of the centering device 6. The centering device 6, and thus the plastic optical waveguide 1, are pressed by a spring against the emission fibers 12 and the detection fibers 14 within a plug-in and coupling element 8. Such a plug-in and coupling element 8 may be a conventional ST plug comprising a bayonet-type lock. The plug-in and coupling element 8 is situated within a hand piece 7. The plastic optical waveguide 1 is pushed back into the coupling portion 3 by the length it protrudes beyond the proximal end of the centering device 6. Since the plastic optical waveguide 1 is fixed or glued within the shaft 2 and/or the distal end of the coupling portion 3, the flexible plastic optical waveguide 1 bends in the space 13 of the coupling portion 3. Due to the bending, the plastic optical waveguide 1 is under tension, which causes the plastic optical waveguide 1 to be permanently pressed against the distal front face of the bundle of emission fibers 12 and detection fibers 14. Thus, there is a permanent physical contact between the plastic optical waveguide 1 and the bundle of emission fibers 12 and detection fibers 14. This guarantees a good coupling of the radiation from the bundle of emission fibers 12 and detection fibers 14 into the plastic optical waveguide 1 and vice versa. At this coupling site, the excitation radiation is coupled from the emission fibers 12 into the plastic optical guide fiber 1. The light leaving distally from the plastic optical waveguide 1 irradiates the root channel under examination which is in the tooth 9. The plastic optical waveguide 1 can be inserted up to the tips of the root channel, since the total diameter of the plastic optical guide wave 1 is smaller than 0.4 mm and the plastic optical waveguide 1 is made to be flexible. The light returned from the irradiated root channel section is received by the distal end of the plastic optical waveguide 1 and is transmitted to a receiving unit 16 via the detection fibers 14 guided within the optical waveguide cable 10. The receiving unit converts the received light radiation into electrical signals. The downstream evaluation unit 20 compares the measured values with stored measured values of healthy teeth and/or infected teeth and a ratio is calculated. This ratio is displayed as values on a display unit 22. The user knows that if this value is smaller than a defined value, the root channel section is free of bacterial residues.

FIGS. 4a and 4b show a light cone of an optical waveguide representing a wide angle optical waveguide and, for comparison, a light cone of a conventional optical waveguide of silica glass which is not a wide angle optical waveguide. The centre axes 34, 36 of both optical waveguides are situated at a distance of 150 μm in parallel with a planar surface 30. The diameters of the optical waveguides are 220 μm each. The wide angle optical waveguide emits light with an opening angle of 95°, corresponding to an acceptance angle of 47.5°. The conventional optical waveguide of silica glass which is not a wide angle optical waveguide has an opening angle of 25°. The maximum light intensities achieved on the planar surface are within the ranges where the lines 35 and 37 meet the planar surface.

The present invention preferably uses a wide angle optical waveguide with an acceptance angle larger than 35°, preferably larger than 40°. Preferably, a plastic material wide angle optical waveguide of polystyrene is used.

FIG. 5 illustrates the light distributions on the planar surface 30 of FIG. 4a and FIG. 4b. The light exit faces of the optical waveguides lie on the abscissa at the value 0. The white points represent the results for conventional optical waveguides of silica glass having an opening angle of 25°, the black squares represent the results for wide angle optical waveguides with an opening angle of 95°. Clear differences between both graphs are visible. An opening angle of only 25° leads to a flat progression of the curve. The maximum light intensity achieved on the planar surface 30 is at about 1.1 mm in front of the optical waveguide having an opening angle of 25°. For an opening angle of 95°, the maximum light intensity achieved on the planar surface 30 is only at about 0.2 mm in front of the optical waveguide. For the wide angle optical waveguide used in the invention, the maximum intensity achieved on the planar surface 30 is more than five times higher compared with the maximum intensity of a conventional optical waveguide of silica glass which is not a wide angle optical waveguide. That is, substantially more accurate measured values can be detected, since the signal-to-noise ratio is much better. As can be seen in FIG. 4a and FIG. 4b, in case of a wide angle optical waveguide, the surface portion examined is much shorter and better illuminated than with conventional optical waveguides of silica glass. The ratio of the bacteria infected surface to the surface examined has a direct influence on the measured values, i.e. if the bacteria infected surface is small as compared with the surface section examined, the infection is only difficult to read from the measured values because of the small percentage of the infected area with respect to the total surface section examined. Small areas of infection are thus easily overlooked if conventional optical waveguides of silica glass are used with large surface sections to be examined and with poor illumination, as can be seen in FIG. 5. For wide angle optical light guides with a rather short surface section and an intensive illumination, the ratio of the surface infected to the surface section examined is more favorable with respect to percentage, so that infected surfaces can be detected in a less ambiguous and more accurate manner. For this reason, the tooth portions to be examined can be examined more accurately, especially in narrow root channels, with a wide angle optical waveguide according to the present invention.

FIG. 6 illustrates the irradiation intensity at the end of different optical waveguide fibers relative to the illumination intensity at the entry of the optical waveguide cable 10 as a function of their lengths. The relative illumination intensity has been calculated from the following formula:

$$B = NA^2 * 10^{-((a*L)/10)}$$

B: illumination intensity
NA: numerical aperture
a: attenuation of the optical waveguide in dB/m
L: length of the optical waveguide in m.

The open circles represent a wide angle optical waveguide with an opening angle of 120°. At about 400 nm, this wide angle optical waveguide has an attenuation of about 17 dB/m. The black points represent an optical waveguide of silica glass with an opening angle of 25°. At about 400 nm, this optical waveguide of silica glass has an attenuation of about 0.1 dB/m.

It is evident from FIG. 6 that long optical waveguides, especially in the context of wide angle optical waveguides, cause an attenuation of the light available at the exit face especially in the short-wave spectral range of about 390-420 nm which is of interest in the excitation of fluorescence. In order to avoid this attenuation, the optical waveguides should have a length of less than 60 cm, preferably less than 10 cm, given that a wide angle optical waveguide is used. In this manner, an illumination intensity about ten times higher than that of conventional optical waveguide of silica glass, which are no wide angle optical wave-guides, could be achieved.

For this reason, a preferred embodiment that is similar to the embodiment in FIG. 3 has the light source 18 arranged within the hand piece 7, see FIG. 7. This has the advantage that the total length of the plastic optical waveguide 1 and of the emission fibers 12 can be made very short, whereby the radiation losses of the excitation radiation can be kept low. The fluorescent radiation excited at the tooth 9 is transmitted from the tooth 9 via the plastic optical waveguide 1 and the detection fiber 14 to a receiving unit 16. The detection fibers 14 are guided in a second optical waveguide cable 26 outside the hand piece 7 to the receiving unit 16.

The invention claimed is:

1. A device for detecting bacterial infection of teeth, comprising:
    a light source;
    a receiving unit;
    an evaluation unit coupled to the receiving unit;
    at least one emission fiber coupled to the light source; and
    at least one detection fiber coupled to the receiving unit,
    wherein the common distal front face of the at least one emission fiber and of the at least one detection fiber is connected with a front face of a single flexible plastic optical waveguide and the diameter of the plastic optical waveguide is less than 400 µm.

2. The device of claim 1, wherein the common distal front face of the emission fibers and the detection fibers and the proximal front face of the plastic optical waveguide are pressed against each other by spring force.

3. The device of claim 1, wherein the plastic optical waveguide has a single coating or multiple coatings.

4. The device of claim 1, wherein the core diameter of the plastic optical waveguide is 300 µm or less, and that the total diameter of the plastic optical waveguide is less than 400 µm.

5. The device of claim 1, wherein the core diameter of the plastic optical waveguide is equal to or larger than the total diameter of the emission fiber and the detection fiber.

6. The device of claim 1, wherein the plastic optical waveguide is made of polystyrene.

7. The device of claim 1, wherein the excitation radiation emitted from the light source via the emission fibers is guided to the tooth by said plastic optical waveguide which also guides the fluorescent radiation coming from the tooth.

8. The device of claim 1, characterized in that the acceptance angle of the plastic optical waveguide is larger than 35°.

9. The device of claim 1, wherein the acceptance angle of the emission fibers and the detection fibers is larger than 35°.

10. The device of claim 1, wherein the emission fibers and the detection fibers, and thus the optical waveguide cable, are flexible.

11. The device of claim 1, wherein the plastic optical waveguide is guided in an inspection probe that comprises a flexible or bent shaft and a coupling portion.

12. The device of claim 11, wherein the distal end of the shaft is blunt.

13. The device of claim 11, wherein the plastic optical waveguide is fixed within the shaft and the coupling portion.

14. The device of one of claim 11, wherein the plastic optical waveguide projects distally from the inspection probe by 1-30 mm.

15. The device of claim 11, wherein the shaft of the inspection probe is 10-30 mm in length.

16. The device of claim 11, wherein the diameter of the shaft is less than 1 mm.

17. The device of claim 11, wherein the shaft is made of metal, or plastic material.

18. The device of claim 11, wherein the coupling portion is a standardized syringe connector.

19. The device of claim 11, wherein the plastic optical waveguide projects freely from the inspection probe by 10-300 mm in the proximal direction.

20. The device of claim 1, wherein the length of the inspection probe is less than 10 cm.

21. The device of claim 11, wherein a centering device is connected with the proximal end of the coupling portion, the plastic optical waveguide being guided in the centering device and projecting centrally from the proximal end of the centering device.

22. The device of claim 21, wherein the plastic optical waveguide projects for at most 2 mm from the proximal end of the centering device.

23. The device of claim 11, wherein a space is provided in the coupling portion, which when the plastic optical waveguide is connected to the emission fibers and the detection fibers, receives an elastically bent portion of the plastic optical waveguide.

24. The device of claim 1, wherein the front faces of the plastic optical waveguide are anti-reflection coated.

25. The device of claim 24, wherein the anti-reflection coating is realized as a moth-eye structure.

26. The device of claim 1, wherein the inspection probe is in the form of a disposable article.

27. The device of claim 1, characterized in that the inspection probe is connected to a hand piece and the junction of the common front face of the emission fibers and the detection fibers and the front face of the plastic optical waveguide is situated within the hand piece.

28. The device of claim 27, wherein the light source is arranged within the hand piece.

29. The device of claim 28, wherein the total length of the at least one emission fiber and the plastic optical waveguide is less than 60 cm.

* * * * *